(12) United States Patent
Garbuzova-Davis et al.

(10) Patent No.: US 9,173,907 B2
(45) Date of Patent: Nov. 3, 2015

(54) METHOD OF PRENATAL ADMINISTRATION OF MAMMALIAN UMBILICAL CORD STEM CELLS FOR THE INTRAUTERINE TREATMENT OF SANFILIPPO SYNDROME

(75) Inventors: Svitlana Garbuzova-Davis, Tampa, FL (US); Paul R. Sanberg, Spring Hill, FL (US); Sylvia Gografe, Nashville, TN (US)

(73) Assignee: University of South Florida, Tampa, FL (US)

( * ) Notice: Subject to any disclaimer, the term of this patent is extended or adjusted under 35 U.S.C. 154(b) by 1787 days.

(21) Appl. No.: 12/168,608

(22) Filed: Jul. 7, 2008

(65) Prior Publication Data

US 2009/0016998 A1 Jan. 15, 2009

Related U.S. Application Data

(63) Continuation of application No. PCT/US2006/047368, filed on Dec. 12, 2006.

(60) Provisional application No. 60/756,257, filed on Jan. 4, 2006.

(51) Int. Cl.
*A61K 35/44* (2015.01)

(52) U.S. Cl.
CPC ........................................ *A61K 35/44* (2013.01)

(58) Field of Classification Search
None
See application file for complete search history.

(56) References Cited

U.S. PATENT DOCUMENTS

| | | | | |
|---|---|---|---|---|
| 5,827,888 A | * | 10/1998 | Abraham et al. | 514/563 |
| 2002/0028510 A1 | * | 3/2002 | Sanberg et al. | 435/368 |
| 2004/0115175 A1 | | 6/2004 | Blau et al. | |
| 2004/0219136 A1 | * | 11/2004 | Hariri | 424/93.71 |
| 2005/0142141 A1 | * | 6/2005 | Pardridge | 424/178.1 |

OTHER PUBLICATIONS

Snyder EY, Taylor RM, Wolfe JH. "Neural progenitor cell engraftment corrects lysosomal storage throughout the MPS VII mouse brain." Nature. Mar. 23, 1995. vol. 374 No. 6520. pp. 367-370.
B D Yandava, L L Billinghurst, E Y Snyder. ""Global" cell replacement is feasible via neural stem cell transplantation: evidence from the dysmyelinated shiverer mouse brain." Proc. Natl. Acad. Sci. U S A. Jun. 8, 1999 vol. 96 No. 12. pp. 7029-7034.
Svitlana Garbuzova-Davis, Sylvia J. Gografe, Cyndy Davis Sanberg, Alison E. Willing, Samuel Saporta, Don F. Cameron, Tammy Desjarlais, Jennifer Daily, Nicole Kuzmin-Nichols, Wilfredo Chamizo, Stephen K. Klasko, and Paul R. Sanberg. "Maternal transplantation of human umbilical cord blood cells provides prenatal therapy in Sanfilippo type B mouse model." The FASEB Journal Express Article. Jan. 2006 vol. 10.
http://www.ggc.org/Diagnostics/Molecular/sanfilippo_syndrome.htm.
Gavin S. Dawe, et al., Cell Migration from Baby to Mother. Cell Adhesion & Migration, vol. 1, Issue 1, (2007). pp. 19-27.
Wikipedia, Efaproxiral. http://en.wikipedia.org/wiki/efaproxiral. Accessed on Nov. 5, 2012.
Svitlana Garbuzova-Davis, et al., Intravenous Administration of Human Umbilical Cord Blood Cells in an Animal Model of MPS III B. The Journal of Comparative Neurology, vol. 515, Issue 93, (2009) pp. 93-101.
Svitlana Garbuzova-Davis, et al., Maternal transplantation of human umbilical cord blood cell provides prenatal therapy in Sanfilippo type B mouse model. The FASEB Joournal, express article, Published online Jan. 9, 2006.
C. Gedeon, et al., Designing Pregnancy Centered Medications: Drugs Which Do Not Cross the Human Placenta. Article in Press, Placenta (2005) pp. 1-8.
YM LO, et al., Two-Way cell traffic between mother and fetus: biologic and clinical implications. bloodjournal. hematologylibrary. org. Blood, vol. 88, No. 11 (Dec. 1, 1996), pp. 4390-4395.
Pacific GM, et al., Placental transfer of drugs administered to the mother. Clin Pharmacokinet, vol. 28, Issue 3, (1995) Abstract.
OpenAnesthesia.org, Pharmacology of the Placenta. http://www.openanesthesia.org/index.php? title=Pharmacology_of_the_placenta. Accessed on Oct. 12, 2012.
PromoCell—Mononuclear Cells. http://www.promocell.com/fileadmin/promocell/kapitelbilder/Mononuclear_Cells_1.jpg and http://www.promocell.com/products/human-stem-and-blood-cells/mononuclear-cells/. Accessed on Nov. 7, 2012.
Kirsi Vahakangas, et al., Drug transporters in the human blood-placental barrier. British Journal of Pharmacology, vol. 158, (2009) pp. 665-678.
Rajendra G. Desai, et al., Maternofetal Passage of Leukocytes and Platelets in Man. Blood; the Journal of Hematology, vol. XXI, No. 6, Jun. 1963, pp. 665-673.
Jeff M. Hall, et al., Detection of Maternal Cells in Human Umbilical Cord Blood Using Fluorescence In Situ Hybridization. Blood, vol. 86, No. 7 (Oct. 1), 1995, pp. 2829-2832.
Joseph Kaplan, et al., Influence of Maternal-Fetal Histocompatibility and MHC Zygosity on Maternal Microchimerism. The Journal of Immunology, vol. 174, (2005) pp. 7123-7128.
Michio Shimamura, et al., Transmission of Maternal Blood Cells to the Fetus During Pregnancy: Detection in Mouse Neonatal Spleen by Immunofluorescence Flow Cytometry and Polymeraase Chain Reaction.
Jim Schroder, Transplacental Passage of Blood Cells. Journal of Medical Genetics, vol. 12 (1975), pp. 230-242.
M. J. Barrett, et al., Accelerated development of immunity following transplantation of maternal marrow stem cells into infants with severe combined immunodeficiency and transplacentally acquired lymphoid chimerism. Clin. Exp. Immunol. (1988) vol. 72, pp. 118-123.

* cited by examiner

*Primary Examiner* — Blaine Lankford
(74) *Attorney, Agent, or Firm* — Robert J. Varkonyi; Smith & Hopen, P.A.

(57) ABSTRACT

A method of treating a fetus or embryo suspected of having a congenital condition that involves an abnormal or missing protein, the method has the steps of a. providing a plurality of human umbilical cord blood in a form suitable for intravenous administration; a b. administering the human umbilical cord blood cells to a mother carrying a fetus of embryo suspected of having said congenital condition. Such congenital conditions include Sanfilippo's syndrome, Hunter's syndrome, Hurler's syndrome, Tay-Sachs disease, Gaucher's disease, von Gierke's disease, Pompes disease, Cori disease, Andersen disease, McArdle's disease, Hers disease, Tauri's disease or Type IX glycogen storage disease.

10 Claims, 3 Drawing Sheets

METHOD OF PRENATAL ADMINISTRATION OF MAMMALIAN UMBILICAL CORD STEM CELLS FOR THE INTRAUTERINE TREATMENT OF SANFILIPPO SYNDROME

CROSS REFERENCE TO RELATED APPLICATIONS

This application is a continuation of prior filed International Application, Serial Number PCT/US2006/047368 filed Dec. 12, 2006, which claims priority to U.S. provisional patent application No. 60/756,257 filed Jan. 4, 2006 which is hereby incorporated by reference into this disclosure.

TECHNICAL FIELD

The subject invention is in the field of medical and veterinarian therapeutics, more specifically, relating to the in utero treatment of congenital or inherited mammalian diseases of fetuses or embryos by the systemic administration of mammalian umbilical cord blood cells or stem cells into the pregnant host (mother).

BACKGROUND

Lysosomal Storage Diseases

Lysosomal storage diseases are a group of uncommon inherited (with rare exception) diseases resulting from defective function within the intracellular lysosome that results in significant clinical morbidity and dysfunctionality as well as premature death. More than thirty different lysosomal storage diseases have been identified and characterized clinically and in many instances pathophysiologically as well. Lysosomes are cytoplasmic membrane-bound, intracellular organelles. These intracellular vesicles contain a variety of glycoprotein hydrolytic enzymes that degrade various macromolecules into their subunits, such as amino, nucleic and fatty acids. The enzymes that are contained within the primary lysosomes are synthesized by the endoplasmic reticulum, and these primary lysosomes may fuse with other intracellular organelles to form secondary lysosomes where macromolecule degradation occurs.

Cell therapy is the transplantation of specialized cells or tissues. It is different from gene therapy, which is a process by which a functional gene or DNA fragment is inserted into key cells to mitigate or cure a disease. Gene therapy in utero is more challenging for researchers because of numerous inherent problems, such as; how to introduce the therapeutic gene across the blood-brain barrier or, how to target the therapeutic gene to one specific area of the body or, how to limit the therapy to the fetal target. However, in utero cell transplantation has been successful in both animals and humans. (See, Muench, M. O. and Barcena, A., "Stem Cell Transplantation in the Fetus," in Cancer Control, 2004, 11(2), 105-118). The inventors herein disclose microchimerism in the fetus can also be achieved using a less invasive method, by intravenously injecting the maternal host with capable cells. This method has the advantage of allowing the earliest possible intervention in addition to avoiding trauma to the fetus.

SUMMARY OF INVENTION

This invention is a method of injecting human umbilical cord blood cells, particularly mononuclear cells, into a pregnant mammal to induce stem cell transmigration into embryos lacking proteins or only capable of synthesizing abnormal protein(s). This invention can be employed in a variety of congenital or inherited disorders, including neurological diseases or disorders, autoimmune diseases or disorders, vascular diseases, and diseases or disorders involving inflammation.

In one embodiment, there is disclosed a method of treating a fetus or embryo suspected of having a congenital condition that is characterized by an abnormal or missing protein. The method has the steps of a. providing a plurality of human umbilical cord blood cells in a form suitable for intravenous administration; and b. administering the human umbilical cord blood cells to a mother carrying a fetus or embryo suspected of having said congenital condition. The congenital condition can be a storage disease. Storage diseases include Sanfilippo's syndrome, Hunter's syndrome, Hurler's syndrome, Tay-Sachs disease, Gaucher's disease, von Gierke's disease, Pompes disease, Cori disease, Andersen disease, McArdle's disease, Hers disease, Tauri's disease or Type IX glycogen storage disease. Other congenital condition is achondroplasia, autism, cerebral palsy, cleft lip, cleft palate, clubfoot and other foot deformities, congenital heart defects, cystic fibrosis, Down syndrome, Fragile X syndrome, genital and urinary tract defects, congenital hearing loss, Marfan syndrome, neurofibromatoses, phenylketonuria (PKU), Rh disease, sickle cell disease, spina bifida or thalassemias. Preferably, the form of human umbilical cord blood cells is that of mononuclear cells obtained from cord blood. Optionally, the method can further include the step of administering an immunosuppressant, including but not limited to cyclosporine A or tacrolimus. Preferably, at least 3 million cells are administered. Preferably, at least 9 million cells are administered. The umbilical cord blood cells can be administered intravenously, intrauterinely or intravaginally.

Lysosomal storage diseases generally are classified by the substances that pathologically accumulate within cells. Chemical classification of lysosomal storage diseases include mucopolysaccharidoses or MPS (e.g., Hurler, Hunter, and Sanfilippo Types III A-D disorders), GM2 gangliosidoses (e.g., Tay-Sach's disease), lipid storage diseases (Fabry's, Gaucher's and Niemann-Pick's diseases), glycoproteinoses (e.g., Sialidosis), mucolipidoses (e.g., ML-III pseudo-Hurler polydystrophy), and leukodystrophies (e.g., Farber's disease). For a more complete listing of known lysosomal storage diseases, see Harrison's Principles of Internal Medicine, (1998) Table 346-1, pp. 2172-3, $14^{th}$ ed, McGraw-Hill Cos., Columbus, Ohio. See Table 1.

TABLE 1

| Classification of Lysosomal Storage Disorders with examples |
| --- |
| Mycopolysaccharidoses (MPS) - SANFILIPPO MPS TYPE III B |
| GM$_2$ liposidoses - TAY SACK'S DISEASE |
| Lipid storage disorders - GAUCHER'S DISEASE |
| Glycoproteinoses - SIALIDOSIS |
| Mucolipidoses (ML) - PSEUDO-HURLER POLYDYSTROPHY |
| Leukodystrophies - FARBER'S DISEASE |

The clinical presentation of a subject with a lysosomal storage disease typically is that of a normal newborn with no apparent suggestion of the underlying disorder. However, these diseases typically are progressive and result in progressive symptomatology, dysfunction and premature death. The clinical course of an affected individual can be predicted by accurate diagnosis and is dependent on the rates of accumulation and degradation of the stored substance. The clinical presentation of lysosomal storage diseases is variable, and in humans includes neurological dysfunction, hepatosplenomegaly, skeletal abnormalities, visual and/or auditory impairment or changes, and differ from one disease to another. The prognosis of patients with lysosomal storage diseases is poor. Excessive morbidity and physical and/or mental disability are anticipated, as is premature death.

Lysosomal storage diseases are generally inherited (exceptions to which are Hunter's syndrome and mucopolysaccharidosis Type II and Fabry's disease, which are X-linked) as autosomal recessive traits. Most humans afflicted with one of these inherited lysosomal storage conditions present with clinical, biochemical and genetic heterogeneity. Reasons for the observed heterogeneity include gene mutations, complete versus partial expression of the mutant gene resulting in complete or partial enzymatic activity, post-translational modifications, inheritance of differing mutant alleles, and variable affinity for substrate(s). Therefore, correlations of the putative genotype do not necessarily result in identical phenotypic expression. Within the lysosomal storage disease group of mucopolysaccharidoses, Sanfilippo syndrome exemplifies the discordance between genotype and phenotypic expression. Sanfilippo syndrome consists of four different genotypes (i.e., MPS III B), each representing a different genetic mutation, but all present with similar clinical signs and symptoms, indicating a level of phenotypic homogeneity. The mucopolysaccharidosis subgroup of lysosomal storage diseases is discussed next.

The group of lysosomal storage diseases known as mucopolysaccharidoses (MPS) diseases, conditions and/or syndromes are characterized by specific enzymatic deficiencies of certain lysosomal enzymes required for glycosoaminoglycan (GAG) catabolism. GAGs, which are major constituents of connective tissue, are long-chain, complex carbohydrates. GAGs are frequently linked to other molecular moieties, including proteins, to form proteoglycans, such as heparan, dermatan, keratin sulfates and certain chondroitins. The clinical features of the mucopolysaccharidoses are the direct result of the accumulation of incompletely or totally undegraded GAGs. The clinical features of each MPS disorder result from the specific enzymatic deficiency, whether fully or partially expressed, and the degree of accumulation of the GAG degradation product (e.g., heparan sulfate in the Sanfilippo syndromes). Accumulation of partially or completely undegraded GAGs results in, depending on the specific MPS disorder, central nervous system disorders (including retardation, seizures, movement disorders, and the like). Other consequences of these diseases include musculoskeletal abnormalities, coarse facies, visual pathology(s), and internal organomegaly(s). Many of these diseases can be diagnosed either via prenatal or postnatal methodologies, described elsewhere in this patent application, and certain MPS disorders have a relatively high prevalence in certain ethnic groups, suggesting the need for appropriate screening and preventative treatment.

The postnatal diagnosis of MPS disorders includes the observation of vacuolated lymphocytes in a peripheral blood smear and the presence of GAGs in the urine. In certain cases, definitive diagnosis of the disorder can be made by specific enzymatic analysis of peripheral blood leukocytes or skin fibroblasts. Prenatal diagnoses are now possible using standard techniques of histopathological analysis of chorionic villous biopsy samples or amniotic fluid cellular material. Data in this patent application relate to Sanfilippo syndrome Type III B; however, these findings are applicable to all lysosomal storage diseases, because the mechanism of action and therapeutic effects are independent of the specific lysosomal storage disorder under consideration.

At present, no known treatments are available to cure the underlying lysosomal storage disease. Certain palliative measures are available and of value, but none cure or eradicate the disease. Therefore, this invention that is the subject of this patent application is of enormous value to afflicted subjects and parents. Please see Table 2 for more detailed information on MPS disorders.

TABLE 2 mucopolysaccharidoses

| 1. DISORDER | ENZYME DEFICIENCY |
|---|---|
| MPS I H, Hurler | alpha-L-Iduronidase |
| MPS I H/s Hurler/Scheie | |
| MPS I S, Scheie | |
| MPS II, HUNTER | Iduronate Sulfatase |
| MPS III, Sanfilippo | |
| TYPE III A | HEPARAN-N-SULFATASE |
| TYPE III B | N-ACETYL-ALPHA-GLUCOS-AMINIDASE |
| TYPE III C | ACETYL-CoA: ALPHA-GLUCOS-AMINIDE N-ACETYLTRANSFERASE |
| TYPE III D | N-ACETYLGLUCOSAMINE-6-SULFATE-SULFATASE |
| MPS Iv, Morquio | n-ACETYLGALACTOSAMINE-6-SULFATE SULFATASE |
| MPS VI, Maroteaux-Lamy | ARYLSULFATASE b |
| MPS VII | BETA-GLUCUORONIDASE |

Sanfilippo syndrome Type III B, or Mucopolysaccharidosis Type III B (MPS III B) is one of four (A, B, C and D) subtypes of lysosomal storage disorders resulting from a failure to degrade heparan sulfate, a glycosaminoglycan (GAG) within lysosomes, by certain enzymes, such as N-acetyl-α-glucosaminidase (Naglu). MPS III B is an autosomal recessive disorder caused by the deficiency of the enzyme N-acetyl-α glucosaminidase (Naglu). The incidence of Sanfilippo syndrome (for all four subtypes) is about 1 in 25,000 births in the United States annually. Approximately two (2) years following birth, human infants begin to develop progressive central nervous system and other multiple organ system abnormalities and dysfunctions. These central nervous system and other organ system abnormalities become manifest as the disease progresses and the storage and degradation of the subject substrate results in accumulation of heparan sulfate. Heparan sulfate and its degradation products are considered to be the basis of the pathophysiologic consequences of MPS Type III B. Prognosis of human patients afflicted with this disease is poor, and therapeutics to reverse or halt the disease are desperately needed. If GAG builds up, the individual becomes more debilitated, including mental retardation. Death usually occurs within the first three decades of life. MPS III B syndrome is caused by mutations in certain genes encoded on chromosome 17q21 (1). Since the original gene was cloned (2, 3), over 90 mutations have been identified and associated with various clinical phenotypes.

A knockout mouse model of MPS III B, demonstrating biochemical abnormalities similar to the human disease, had been treated by disrupting the Naglu gene responsible for heparan sulfate degradation (4). The homozygous mutant mice are healthy and fertile at a young age and typically survive 8-12 months. Disease symptoms become obvious after approximately 6 months of age. As early as the first month of age, pathological changes, such as vacuolated macrophages, have been observed in the liver, spleen, lymph nodes, kidney, lung, and skin. Neurons are also affected in many parts of the central nervous system.

Diagnosis of MPS Type III B is currently based on clinical features and urinalysis for heparan sulfate. Enzyme assay testing of cultured skin fibroblasts and leukocytes for enzyme deficiency are also used to provide a definitive diagnosis of MPS III B (5). Prenatal diagnosis in humans can be performed as early as 9-16 weeks of gestation using chorionic villus biopsies and/or amniotic fluid cells to ascertain whether or not the fetus/embryo has Sanfilippo type A (6), B (7, 8), C (9) or D (10).

At present treatment of patients with MPS is symptomatic, preventative or curative treatments are not available. Enzyme replacement therapy is a possible treatment and has been attempted by bone marrow transplantation. In some patients receiving bone marrow transplantation, the replacement of enzymatically deficient blood cells led to significant clinical improvement with complete arrest of the progressive disorder (MPS VI) or improved developmental outcome (MPS I) (11, 12). However, bone marrow transplantation did not cause neurological regression in patients with Sanfilippo (MPS III B) or Hunter (MPS II) syndromes (11,13). Since bone marrow transplantation only arrests symptom progression, treating patients in the earliest stages of the disease may display improved outcomes or even reversal of the disease, the most desired outcome.

BRIEF DESCRIPTION OF FIGURES

FIG. 1a shows many MNC hUCBCs (green, asterisks) in the decidua. Some cells were established in the spongiotrophoblast layer (FIG. 3a), labyrinth (FIG. 4a) and chorionic plate (FIG. 5a). Scale bar in FIGS. 1a, 3a, 4a and 5a is 50 μm.

Figure 1:
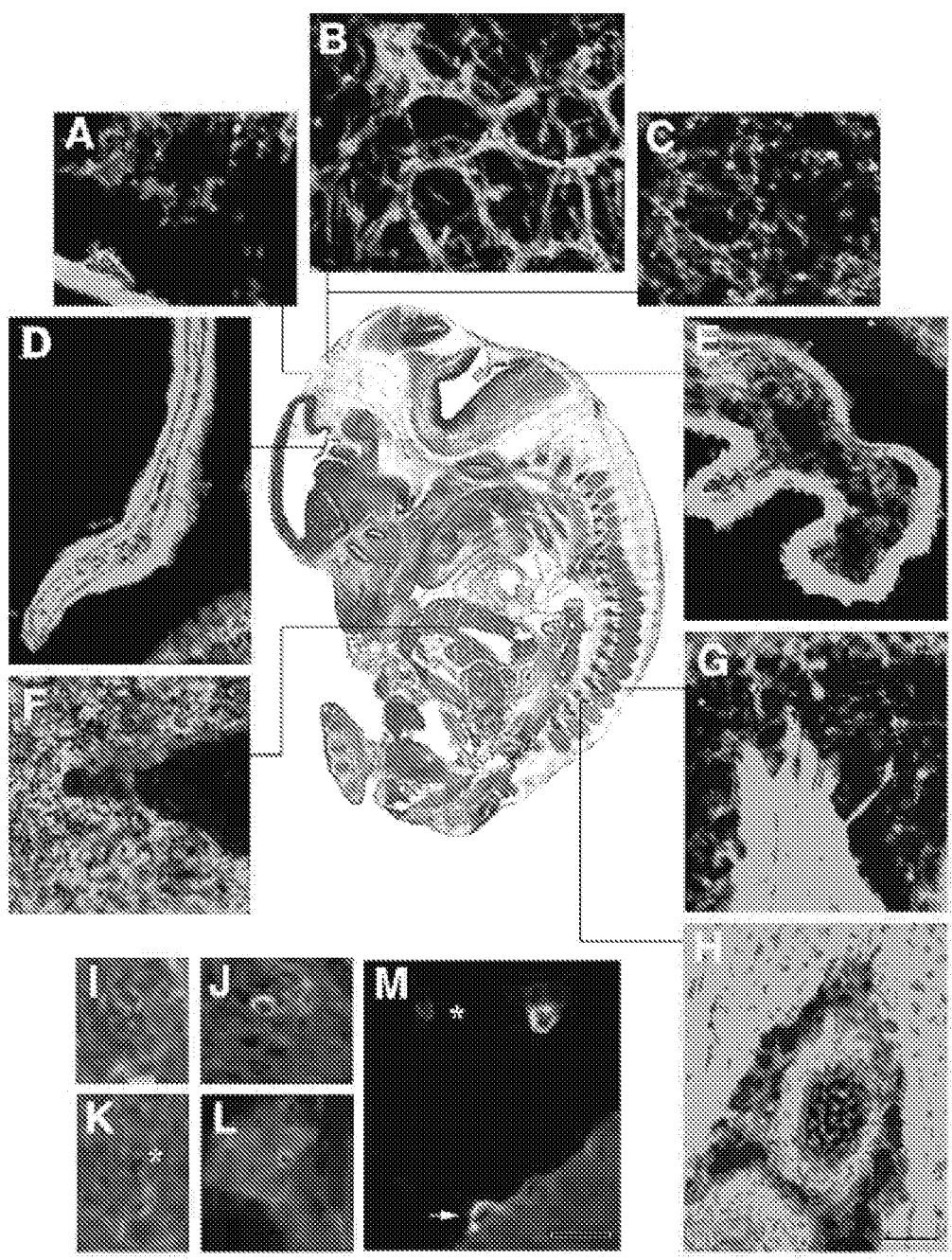
FIG. 1 displays the distribution of MNC hUCBCs in mouse embryos (E12.5) at one week after cell administration into a heterozygous Sanfilippo mother on the fifth day of pregnancy. The central embryo was stained using cresyl violet. The MNC hUCBCs can be identified by the FITC labeled antibody specific for human nuclear antigen. Many cells were found in primitive ectomeninx (FIG. 1A) and loosely packed cephalic mesenchyme (FIGS. 1B and 1C). Some cells were located in choroid plexus extensing into the lateral ventricle (FIG. 1D) and in the choroid plexus differentiating from the roof of the fourth ventricle (FIG. 1E). Cells also were identified in areas around the dorsal root ganglion (thoracic vertebral body) (FIG. 1G) and cargilage primordium (lumbar vertebral body) (FIG. 1H). Numerous cells were found in the fetal liver (FIG. 1F). The scale bar in FIG. 1H is 50 μm, which is the same magnification in FIGS. 1A-1H. Some cells were CD34 positive in the embryo liver (green/red) (FIG. 1I). An asterisk indicates negative staining of cell for CD34 in the liver (FIG. 1K). Expression of CD117 was found in some cells in the mantle (FIG. 1J) and marginal layers of the spinal cord (green/red) (FIG. 1L). Cells doubly positive for HuNu and CD117 antigens were also found in the fourth ventricle (green/red) (FIG. 1M). Cells attached to the ventricle wall displayed epithelial-cell morphology (arrow). An asterisk shows negative expression for CD117. The scale bar in FIG. 1M is 25 μm, the same magnification in FIGS. 1I-1M.

The following written description provides exemplary methodology and guidance for carrying out many of the varying aspects of the present invention.

DETAILED DESCRIPTION

Maternal cells have recently been discovered to pass into the fetus during pregnancy in human, mammalian and other animal models. However, functional benefits of maternal microchimerism in utero are unknown. Here we have taken advantage of this route for prenatal delivery of α-N-acetylglucosaminidase (Naglu) enzyme into the enzyme-deficient mouse model of Sanfilippo syndrome type B (MPS III B). Enzymatically sufficient mononuclear cells (MNC) from human umbilical cord blood (hUCB) were administered intravenously into heterozygous females previously mated with heterozygous males on the 5$^{th}$ day of pregnancy during implantation of blastocysts in this murine model. The major findings were as follows: 1) administered MNC hUCBCs transmigrated and diffused into the embryos/fetuses (E12.5); 2) some transmigrated cells expressed CD34 and CD117 antigens, blood cell precursors and stem cells, respectively; 3) transmigrated cells were found in both the maternal and embryonic parts of placentas; 4) transmigrated cells corrected Naglu enzyme activity in all embryos; 5) administered MNC HUCBCs were extensively distributed in the organs and blood of heterozygous mothers at one week after transplantation. Results indicated that prenatal delivery of Naglu enzyme by MNC hUCBC administration into mothers of enzyme-deficient embryo mice raises the enzyme level and may present a significant opportunity for new biotechnological therapeutics, including, but not limited to autologous or xenotransplantations or derivatives thereof to treat many inherited disorders in humans and mammals.

Herein we disclose prenatal delivery of the missing enzyme for the treatment of MPS III B. The long-established dogma of restricted materno-fetal cell passage through the placental barrier is now being re-examined. Reported studies in humans (14-20) and experimental (mostly murine models (21, 22) or pregnancy have shown cell exchanges between the maternal and fetal circulations without classical signs or symptoms of incompatibility or rejection. Maternal cells were found in 20% of examined cord blood samples from male babies; 14% of maternal cells were T-lymphocytes (T-cells) and 4% of cells were CD34 positive (14) early stage hematopoietic cells. Conversely, fetal cells passed into the maternal circulation during pregnancy (15-18). It has been shown that fetal lymphocytes passed actively into the mother's blood relative early (15 weeks' gestation) (17). Moreover, fetal cells transferred to the mother may develop the multilineage capacity to differentiate into epithelial and hepatic cells within maternal tissues (18), such plasticity of stem cells is an unexpected finding. Such bilateral trafficking of nucleated cells between the fetus and the mother has been detected in separated as well as the same feto-maternal pairs using sensitive PCR-based tests (19). There fetal-derived DNA sequences were found in maternal peripheral blood in 26 of 51 cases (51%); whereas, maternal DNA sequences were detected in 16 of 38 cases (42%) of the umbilical cord samples, higher than previously described (14). Interestingly, bilateral cell traffic was established in 28 cases. In animal studies, transplacental traffic of nucleated maternal cells was established in mouse scid/scid fetuses at 12.5 gestational day (gd) or in offspring with normal lymphoid development at 16.5 gd (21). Predominantly, maternal cell chimerism was observed in fetal bone marrow and some cells were detected in the postnatal spleen. Another interesting study using molecular techniques demonstrated that maternal T-cells of immunized pregnant mice crossed the placenta into the fetus and induced antigen-specific immunological tolerance in the offspring (22). Although the mechanism of two-way, materno-fetal and feto-maternal cell bilateral passage through the placenta was still unknown, it was suggested that this phenomenon could be due to developing immunotolerance between the mother and the fetus (14,20) or to "help the fetus to build a better defense system" (22). Either passive or active bilateral cell trafficking might occur at delivery or during prenatal development (14,19). However, it is clear that the immunological relationship between mother and fetus plays an important role in materno-fetal immune recognition. Presently studies are focusing on the critical features of the immune system responses of mother and embryo/fetus during normal pregnancy (23-25), or, in the course of pathological conditions, such as autoimmune diseases (26, 27).

This emerging evidence of nucleated maternal cell trafficking into fetal circulation prompted us to test a new therapeutic prenatal strategy. If the transplantation of enzymatically sufficient cells into a mother's blood circulation allows their migration into the MPS Type III B fetus, the migrating cells could replace the missing enzyme. Human umbilical cord blood cells (hUCBCs) may be preferable to other cell sources to accomplish this task. Compared to bone marrow cells, hUCBCs have a more immature morphology of the myelocytic/monocytic cells, smaller numbers of mature neutrophils and unique ultrastructural elements, such as nuclear pockets in the neutrophils, which accelerate the transport of RNA to the cytoplasm (28). Hematopoietic progenitors from hUCBCs are rich in the most primitive stem cells (29-31). Moreover, the immune immaturity of hUCBCs can help reduce the risk of graft-versus-host disease after transplantation (32, 33). Recently hUCBC transplants from unrelated donors were shown to improve neurocognitive performance and decrease somatic features in patients with Hurler's syndrome (MPS I) (34). More recently, we showed that mononuclear hUCBCs contain and release Naglu enzyme in vitro (35). When these enzymatically sufficient cells were administered into the lateral cerebral ventricle of 1-month-old mice modeling MPS III B, they prevented histopathological changes, probably due to replacement of the deficient Naglu enzyme (35). Transplanted hUBCBs survived long term (7 months), migrated into the parenchyma of the brain and expressed neural antigens and exhibited neuron- and astrocyte-like morphology. Transplant benefits were also demonstrated by stable cytoarchitecture in the hippocampus and cerebellum and by reduced GAGs in the livers of treated mutant mice. These findings suggest that hUCBC may have therapeutic potential for enzyme delivery in MPS III B. Transplantation of hUCBCs early in the disease may further improve results, or even prevent the disease directly or at least the clinical manifestations of the disease.

Throughout this application, various publications are referenced. The disclosures of all of these publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

EXAMPLES

Animals

All animals used in the study were obtained from the USF established colony of Naglu mice developed from heterozygous Sanfilippo Type B B6.129S6-Naglu$^{tm1fn}$ breeding pairs (The Jackson Laboratory, Bar Harbor, Mass.). The first generation (F1) was obtained from these breeding pairs by crossing male with female (both heterozygous) to produce littermates of three phenotypes: homozygote, heterozygote and wild-type. Phenotyping of all animals were performed by enzyme assay The five mating pairs of these heterozygous Naglu mice and two pairs C57BL/6 (control) at 7-8 weeks of age were used for the study. All mice had been maintained on a 12:12 hr dark:light cycle and given food and water ad libitum.

This was the first pregnancy for all female mice in the study. To obtain timed pregnancies, females were paired with males in the afternoon prior to the end of the light cycle. On the following 3 days, females were examined early in the morning for the presence of a copulatory vaginal plug (a mixture of secretions of the vesicular and coagulating glands of the male). The plug usually fills the vagina from cervix to vulva. The first day of gestation, stage E0.5, was considered to be the day the plug was found.

hUCBCs were prepared for transplantation on the 5$^{th}$ day of pregnancy. Cryopreserved mononuclear (MNC) human umbilical cord cells (hUCBCs) (Saneron CCEL Therapeutics, Inc., Tamps, Fla.) from unrelated donors were thawed rapidly at 37° C., then transferred slowly with a pipette into a 15-mL centrifuge tube containing Isolyte S, pH 7.4 (Braun/McGaw Pharmaceuticals).

Prenatal delivery of MNC hUCBCs was performed on the 5$^{th}$ day of pregnancy (embryonic stage E5.5). The MNC hUCBCs or medium ($3 \times 10^6$ cells in Isolyte S or Isolyte S alone) to mothers under anesthesia with isofluorane (2-5% in 2 L $O_2$/min). The jugular vein was exposed and isolated using blunt dissection. The vein was ligated and a hole was made with a 26 gauge needle. A 31 gauge needle attached to a 10 µL Hamilton syringe was placed into the lumen of the vein and sutured in place. The cells or medium were delivered over 5 min. The needle was withdrawn, the suture tightened, and the incision closed. Females receiving hUCBCs were immunosuppressed with cyclosporine A (20 mg/kg orally per day) during the post-transplantation period. The mothers of four litters totaling 29 embryos intravenously received cells and one mother of 9 embryos received media. Two additional litters of 14 embryos (No-Tx group) from C57BL/6 pregnant females did not receive cells or medium injection. Seven days after the injections, heterozygote females were euthanatized and embryos (E12.5) and related placentas were removed for identification of transmigrated hUCB cells by immunohistochemistry and Western immunoblot analysis. Embryos from one randomly selected transplanted heterozygote female were used to determine Naglu enzyme activity. Embryos, including placentas, from C57BL/6 females were removed at the same embroyinc state (E12.5) and used as controls. The brains and organs from transplanted females were also removed for immunohistochemical analysis of administered cell distribution.

Seven days after the injections, heterozygous females were euthanatized and embryos (E12.5) and related placentas were removed for identification of transmigrated hUCBCs by immunohistochemistry and Western immunoblot analysis. Embryos from one randomly selected transplanted heterozygous female were used to determine Naglu enzyme activity. Embryos, including placentas, from C57BL/6 females were removed at the same embryonic state (E12.5) and used as controls. The brains and organs from transplanted females were also removed for immunohistochemical analysis of administered cell distribution. Female mice were anesthetized with sodium pentobarbital (60 mg/kg ip) and perfused transcardially with 4% paraformaldehyde in 0.1 M phosphate buffer (PB; pH 7.2). The embryos, placentas and mother's organs were post-fixed and then cryoprotected in 20% sucrose in 0.1 M PB overnight. Sagittal sections were cut at 30 μm in a cryostat. Serial sections were thaw-mounted on slides, washed with deionized water to remove the freezing medium and then rinsed several times in PBS. The hUCBCs were identified by the human-specific market as we described previously (41). Briefly, the primary mouse monoclonal anti-human nuclei (HuNu, 1:50, Chemicon, Temecula, Calif.) antibody was pre-incubated with a monovalent goat anti-mouse Fab fragment antibody conjugated to FITC (1:200, Jackson Immunoresearch, West Grove, Pa.). After blocking the tissue for 30 min, this antibody complex was applied to the tissue sections and incubated overnight at 4° C. After rinsing a few times in PBS, the sections were double immunostained with mouse monoclonal anti-human antibodies for CD34 (1:50, Santa Cruz Biotech, Santa Cruz, Calif.) and stem cell factor receptor (CD117, c-kit receptor, 1:100, Spring Bioscience, Fremont, Calif.). The next day, the slides were incubated with goat anti-mouse secondary antibody conjugated to rhodamine (1:1000, Alexa, Molecular Probes, Invitrogen, Carlsbad, Calif.) for 2 hr. After several rinses in PBS, the sections were coverslipped with Vectashield DAPI (Vector Laboratories, Burlingame, Calif.) and examined under epifluorescence using an Olympus research microscope.

HUCBCs were observed in the brains and abdominal organs in females one wk after they received the cells. Cells identified by HuNu specific antigen expression were found inside and outside the CNS. HUCBCs were identified in the brain (cerebral cortex, hippocampus, choroid plexus and striatum) and organs (heart, lung, kidney and spleen). Although most grafted cells were found in the blood vessels of the aforementioned organs, some also were observed in the parenchyma.

Embryos and placentas (n=11) from two randomly selected hUCBC-treated females were analyzed for the presence of transmigrated cells, using the HuNu marker for anti-human nuclei. The embryo/placenta units (n=8) from medium-injected heterozygous females and C57BL/6 females served as controls. Morphological analyses of embryos and placentas were also performed. Examination revealed transmigration of hUCBCs into many areas and parts of the embryos (FIG. 1). Mainly, the cells were present in the primitive ectomeninx (FIG. 1A), the loosely packed cephalic mesenchyme (FIGS. 1B and 1C), the choroid plexus extending into the lateral ventricle (FIG. 1D), and the choroid plexus extending from the roof of the fourth ventricle (FIG. 1E). Cells were found in areas around the dorsal root ganglion (FIG. 1G) and the cartilage primordium of the vertebral body (FIG. 1H). Many cells were identified in the embryo liver (FIG. 1F), and some were CD34 positive (FIG. 1I). CD117 was found in some cells in marginal or mantle layers of the spinal cord (FIGS. 1J, L). Cells doubly positive for HuNu and CD117 antigens also were found in the fourth ventricle. Interestingly, a cell attached to the ventricle wall displayed epithelial-like cell morphology (FIG. 1M). Notably, no morphological abnormalities were found in fetuses from mothers receiving hUCBCs, and their developmental features at this state (E12.5) were similar to fetuses from medium-injected heterozygotes or C547BL/6 females.

Western Immunoblot

For additional identification of hUCBCs, Western immunoblot assay was used on the embryos and placentas from the three types of offspring (cell transplanted, medium injected and C57BL/6 control). hUCBCs ($10^7$), after several washes in PBS, were used as an assay control. A homogenizer was used to extract proteins in a homogenization buffer containing 20 mM Tris (pH 8.0), 1 mM EDTA, 1 mM dithiothreitol, 0.5 mM spermine, 0.5 mM spermidine, 50% glycerol and protease inhibitors. Homogenates were rocked for 30 min after addition of 1/10 volume of 2.5 M KCl and spun at 14000 rpm for 30 min. Protein concentration was measured using the bicinchoninic acid (BCA) method. Proteins extracted from different embryo tissues were separated on a 12% SDS-PASGE gel and transferred onto a nitrocellulose membrane using a Biorad (Hercules, Calif.) Semi-Dry Transblot technique according to the manufacturer's instructions. The membranes were blocked overnight at 4° C. in a solution containing 5% dry milk and Tris-buffered saline (TBS) composed of 200 mM NaCl and 50 mM Tris-HCl (pH 7.4) and supplemented with 0.04% Tween-20. The membranes were rinsed in TBS-Tween mixture and incubated overnight at 4° C. with primary HuNu using 1:50 dilution by 1% dry milk prepared in TBS-Tween. After washing 3× for 10 min with TBS-Tween at 4° C., the membranes were incubated with anti-mouse secondary antibody conjugated with horseradish peroxidase (1:2000 Santa Cruz Biotechnology) for 1 hr at room temperature. The blot was developed by ECL Western blotting detection kit (Amersham, Piscataway, N.J.).

Naglu enzyme assay was performed in all fetuses (n=5, E12.5) from one randomly chosen litter whose heterozygous mother received hUCBCs. Naglu enzyme activity was similar in all embryos, ranging from 1.203-1.355 nmol/h/protein, which was also similar to their parents (Table 3). The level of enzyme detected in heterozygous parents at 2 mo of age, 1 wk before cell administration, was 1.035 nmol/h/protein in females and 1.369 nmol/h/protein in males.

TABLE 3

Naglu Enzyme Activity in Embryos (E12.5) at One Week After Cell Administration into Mother at 5th Day of Pregnancy.

| Subject | Naglu Enzyme Activity (nmol/h/protein) |
|---|---|
| Embryo 1 | 1.264 |
| Embryo 2 | 1.355 |
| Embryo 3 | 1.031 |
| Embryo 4 | 1.154 |
| Embryo 5 | 1.203 |

Histology

For histological analysis of embryos and placentas, routine paraffin processing was performed on tissues. Paraffin sections were cut at 5 μm intertals. Embryonic tissues were stained with 0.1% cresyl violet. Hematoxylin and eosin staining was performed on the placentas.

Gross Necropsy

The pregnant uterus, placenta and embryos were dissected following a standardized technique described by Ward and Devor-Henneman (36) to minimize variability. The number of normal placental sites as well as sites of spontaneous resorption/dead embryos in each mother were counted and crown-to-rump length of each embryo was measured. Additionally, placenta size in all three dimensions (length, width, thickness) was determined. The entire uterine horns, the yolk sac, placenta and embryos themselves were carefully inspected and observations were recorded. There were no undeveloped or dead embryos in the litter chosen for Naglu testing.

Figure 2:
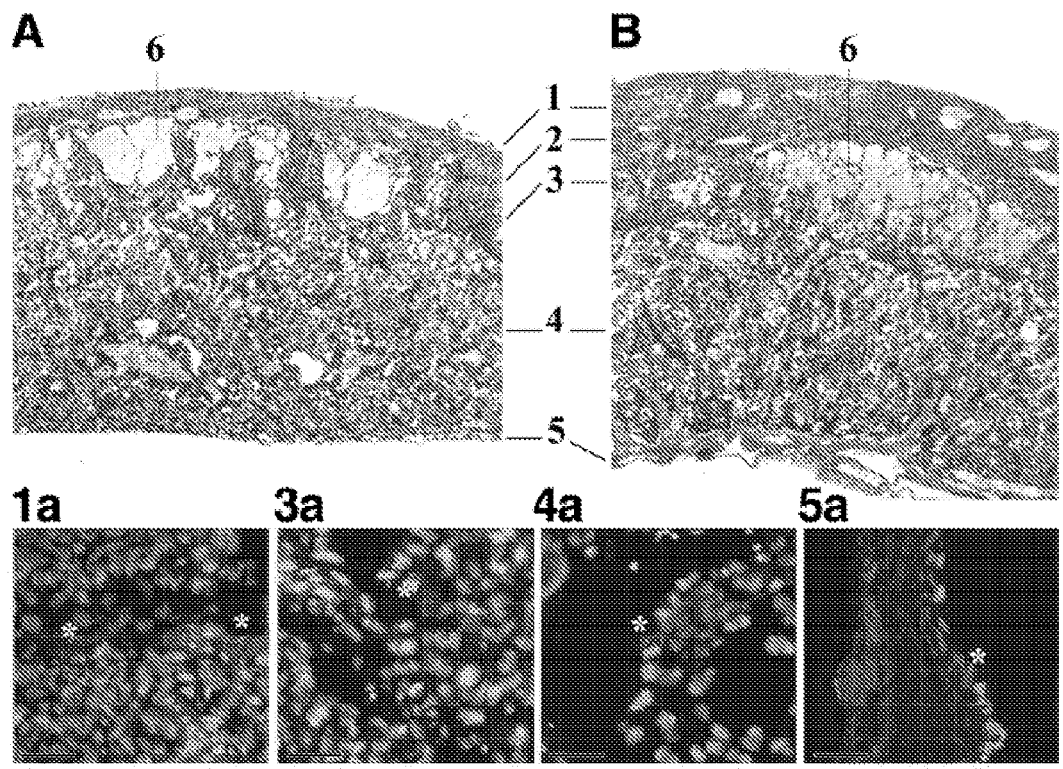
FIG. 2 is a set of photomicrographs, showing a heterozygous placenta on the left (a) and a control C57BL/6 control uterus on the right (b). Magnification is 100×. The placental thickness is considerably less on the left, mainly due to the smaller decidua (layer 1) and chorionic plates (layer 5). Other layers are the giant cells (layer 2), spongiotrophoblast (layer 3), labyrinth (layer 4) and vascular space (layer 6). The four figures in a row highlight MNC hUCB cells in various layers.
Figure 3:
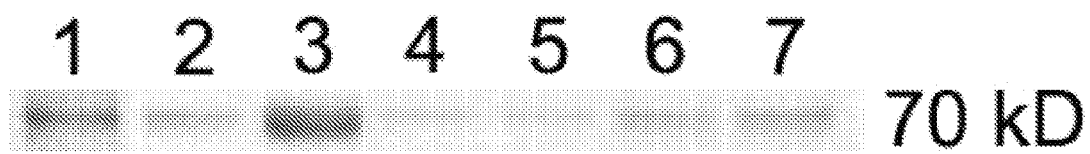
FIG. 3 is a photograph of a Western immunoblot of proteins extracted from mice embryos (E12.5). The 70 kd protein is mouse anti-human nuclei monoclonal antibody (HuNu). Lane 1 demonstrates specific positive bands of MNC hUCBCs (positive control). Lane 2 is negative in the placenta of an embryo after cell Administration to the mother, similar to the placenta of negative control C57BL/6 (lane 4) and Naglu mice receiving medium (lane 5). The intense band in lane 3 is from a mouse embryo one week after its mother's treatment with MNC hUCBCs. Lanes 6 and 7 are negative for mouse HuNu in control C57BL/6 embryo and Naglu embryo receiving medium, respectively.
Figure 4:
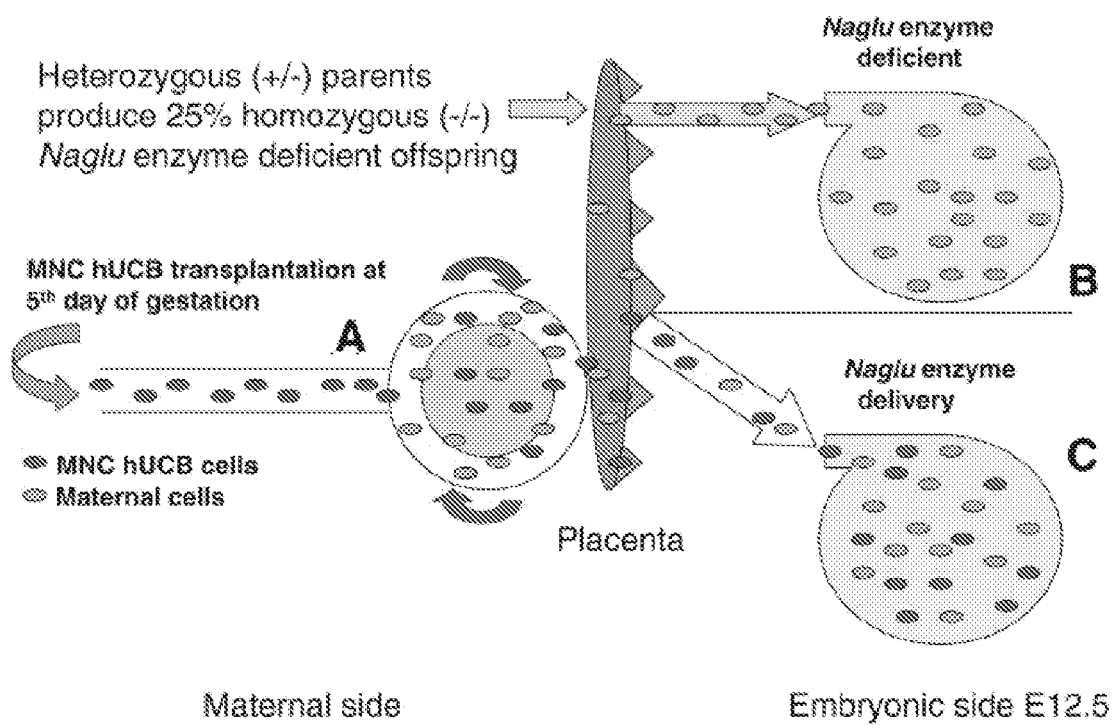
FIG. 4 is a schematic diagram of prenatal delivery of by transplantation of enzymatically sufficient MNC hUCBCs into the blood circulation of a mouse modeling MPS III B (Naglu enzyme deficient). Transplanted cells into the heterozygous mother at the 5$^{th}$ gestation day (A) transmigrated to the developing embryos (E12.5) and corrected Naglu enzyme activity (C). Note: the mating of heterozygous mouse parents usually produced ~25% Naglu (−/−) deficient homozygous offspring (B).

After dissection of the mouse uterus at 12.5 gd, embryos and placentas were examined. Table 4 provides a numerical tabulation regarding viable/nonviable fetuses and morphometric characteristics of embryos/placentas in each group.

derived labyrinth, spongiotrophoblast, and giant cell trophoblast of the heterozygous females were within normal limits. The labyrinth is comprised mainly of embryonal labyrinth trophoblasts, embryonal endothelium-forming blood vessels and maternal blood cells. Immunohistochemical staining for hUCBCs demonstrated their presence in the deciduas of the treated heterozygous females (FIGS. 1, 1a). Some cells were observed in the spongiotrophoblast layer (FIGS. 2, 3a), labyrinth (FIGS. 2, 4a) and the chorionic plate (FIGS. 2, 5a).

Statistics

Data have been presented as means±standard errors of the means based on a normal Gaussian distribution (i.e., the bell-shaped curve). The one-way ANOVA with Newman-Keuls Multiple comparison post-hoc test was used. The ANOVA test assumes that the data were sampled from populations with Gaussian distributions. This assumption was tested using the Kolmogorov-Smirnov test (KS-test) which has no assumption about the distribution of data.

Discussion

TABLE 4

Gross Necropsy Examination of E12.5 Embryos and Placentas After Prenatal Delivery of MNC hUCBCs or Medium into Heterozygote Naglu mice and No-Treatment (No-Tx) Wild Type C57BL/6 Mice.[a]

| Treatment | Total # of Embryos | Undeveloped or Dead Embryos/ Percent | Crown-to-Rump Length of Embryos (mm) | Placenta Size Length (mm) | Placenta Size Width (mm) | Placenta Size Thickness (mm) |
|---|---|---|---|---|---|---|
| MNC hUCB Naglu +/− | 29 | 4/13.8% | 9.18 ± 0.03 | 7.19 ± 0.05** | 6.67 ± 0.06 | 1.80 ± 0.03* |
| Medium Naglu +/− | 9 | 1/11.1% | 9.44 ± 0.09 | 7.28 ± 0.10** | 7.11 ± 0.10 | 1.99 ± 0.05*?? |
| No-Tx C57BL/ 6+/+ | 14 | 2/14.3% | 9.43 ± 0.04 | 8.49 ± 0.04 | 7.44 ± 0.03 | 2.33 ± 0.03 |

[a]Data are presented as mean (±s.e.m.). No significant differences were found in crown-to-rump lengths of treated (MNC hUCB Naglu +/−) or non-treated (medium Naglu +/−, No-Tx C57BL/6 +/+) embryos. Length of placenta from either cell-treated or medium-treated Naglu embryos were significantly less (**p < 0.001, ANOVA) less than those from C57BL/6 embryos. The placental thickness of placenta from cell-treated embryos was significantly less (*p < 0.01, ANOVA) and tended to be less from medium-treated Naglu embryos compared with C57BL/6 embryos.

The number of embryos and embryo crown-to-rump lengths did not differ between heterozygote offspring receiving hUCBCs or medium or between the heterozygote offspring and the C57BL/6 control females. Intrauterine embryonic death, common in placental mammals, was observed in the heterozygotes receiving cells (13.8%) or medium (11.1%), as well as C57BL/6 females (14.3%). No dead embryos were detected in two heterogygous females that received hUCBCs. Examination showed normal placental development (full red color, vascular expansion) in all embryos, except for the dead fetuses, which presented as amorphous masses. No further examination of these latter embryo/placental masses was pursued since intrauterine mortality, up to 20%, is considered normal (36,37). Although no gross abnormalities were noted in placentas, the length and thickness of placentas from heterozygous females were significantly less than those from C57BL/6 mice (Table 4).

Placentas from both heterozygote and C57BL/6 females appeared structurally normal (FIGS. 2a and b, respectively). However, the placental thickness in heterozygous females was significantly reduced compared to control C57BL/6 mice. This difference was due to decreased thickness of the decidua (the maternal part) in the heterozygous females, as shown in FIG. 2a. Also the chorionic plate in this mouse was thinner. Structural characteristics of the embryonically We have proven that hUCBCs injected into the systemic circulation of heterozygous females modeling MPS III B on the 5th day of pregnancy transmigrated and diffused into embryos, as determined 7 days later (E12.5). Some transmigrated hUCBCs expressed CD34, which is associated with human hematopoietic progenitor cells, and CD117, which has been associated with stem cells, among other cell types. Transmigrated hUCBCs were found in both the maternal and embryonic parts of the placentas. Naglu enzyme activity was similar in all embryos and similar to the level of their heterozygous females and males at one week before transplantation. Because with two heterozygous parents, there was a 25% chance of homozygous (−/−) enzyme in the offspring, in which case no intrinsic Naglu would be present, this result supports our inference that the hUCBCs helped increase the level of Naglu.

Besides replacing Naglu, the data support the use of umbilical cord blood cells for other lysosomal storage diseases, other storage diseases, as well as other congenital or inherited conditions.

Example 2

In a follow-up study, we investigated if mononuclear cells derived from human umbilical cord blood (MNC hUCB) transplanted into additional pregnant female mice modeling Sanfilippo Syndrome Type B at the 5$^{th}$ day of pregnancy could correct enzyme deficiency in offspring at birth. This differed from the preceding study in which gestation was interrupted at the seventh day after MNC hUCBC transplantation. Again both parents were heterozygous for the mutation. All pups were euthanatized at 1-2 hours after birth. The normal distribution of pup phenotypes from heterozygote parents is: 50% heterozygote, 25% wild type, and 25% homozygote. Results showed that phenotype distribution in pups from control non-treated mother (#24C, see Table 5) was 60% heterozygote, 20% wild type, and 20% homozygote. When we transplanted 3×10$^6$ MNC hUCB cells into mother #21, enzyme activity was not corrected in newborn pups (45% heterozygote, 22% wild type, and 33% homozygote). With an increased dose of 9×10$^6$ cells we completely corrected enzyme activity in the offspring of mother #25 (60% heterozygote and 40% wild type). No homozygous pups were identified from this mother. Another mother (#27) receiving 9×10$^6$ cells had 56% heterozygote, 33% wild type, and only 11% homozygote pups. In other words, only one pup from mother #27 had uncorrected enzyme levels, rather than the expected 2-3 pups from this litter size.

intended to be in the nature of description, rather than limitation. Obviously, many modifications and variations of the present invention are possible in light of the above teachings and one of ordinary skill in the art, in light of this teaching, can generate additional embodiments and modifications without departing from the spirit of or exceeding the scope of the claims of this invention. Therefore, it is to be understood that within the scope of the appended claims, the invention may be practiced otherwise than as specifically described. Accordingly, it is to be understood that the drawings and descriptions herein are proffered by way of example to facilitate comprehension of the invention and should not be construed to limit the scope thereof.

REFERENCES

1. Neufeld E F and Muenzer J (1995) The mucopolysaccharidoses. In THE METABOLIC AND MOLECULAR BASES OF INHERITED DISEASE (Scriver C R et al eds) 7$^{th}$ ed, Vol II, pp 2365-94, McGraw-Hill, New York City.
2. Zhao H G H et al (1996) Proc Natl Acad Sci USA 93:6101-5.

| Mom ID | Enzyme mom/dad | Newborn pup ID | Treatment | # Newborn pups pups | # Newborn pups FD | Enzyme activity | phenotype |
|---|---|---|---|---|---|---|---|
| #24c | 2.9/2.7 | Pup 1 | No | 10 | 4 | 3.842 | Hetero |
| | | Pup 2 | Transplant | | | 3.240 | Hetero |
| | | Pup 3 | | | | 0.611 | Homo |
| | | Pup 4 | | | | 2.834 | Hetero |
| | | Pup 5 | | | | 2.767 | Hetero |
| | | Pup 6 | | | | 6.500 | Wild Type |
| | | Pup 7 | | | | 3.553 | Hetero |
| | | Pup 8 | | | | 4.834 | Wild Type |
| | | Pup 9 | | | | 3.134 | Hetero |
| | | Pup 10 | | | | 0.194 | Homo |
| #21 | 1.1/3.7 | Pup 1 | 3 × 10(6) | 9 | 1 | 1.848 | Hetero |
| | | Pup 2 | Cells | | | 5.231 | Wild Type |
| | | Pup 3 | | | | 2.105 | Hetero |
| | | Pup 4 | | | | 1.680 | Hetero |
| | | Pup 5 | | | | 4.790 | Wild Type |
| | | Pup 6 | | | | −.0150 | Homo |
| | | Pup 7 | | | | 1.509 | Hetero |
| | | Pup 8 | | | | −0.320 | Homo |
| | | Pup 9 | | | | −0.800 | Homo |
| #27 | 2.7/2.8 | Pup 1 | 9 × 10(6) | 9 | 0 | 4.117 | Hetero |
| | | Pup 2 | Cells | | | 2.810 | Hetero |
| | | Pup 3 | | | | 5.723 | Wild Type |
| | | Pup 4 | | | | 5.224 | Wild Type |
| | | Pup 5 | | | | 4.281 | Hetero |
| | | Pup 6 | | | | 2.850 | Hetero |
| | | Pup 7 | | | | G | Homo |
| | | Pup 8 | | | | 5.648 | Wild Type |
| | | Pup 9 | | | | 2.747 | Hetero |
| #25 | 2.8/2.7 | Pup 1 | 9 × 10(6) | 5 | 1 | 4.208 | Hetero |
| | | Pup 2 | Cells | | | 5.323 | Wild Type |
| | | Pup 3 | | | | 5.961 | Wild Type |
| | | Pup 4 | | | | 3.142 | Hetero |
| | | Pup 5 | | | | 2.843 | Hetero |

CONCLUSION

Prenatal delivery of MNC hUCBCs into pregnant female mice modeling Sanfilippo syndrome Type B at the 5$^{th}$ day of pregnancy corrected Naglu enzyme deficiency in offspring at birth. This benefit was dose dependent. Also, it appears that the probability of enzyme correction may be affected by the mouse litter size, with pups in smaller litters being more likely to have their enzyme deficiency corrected.

This invention has been described in an illustrative manner, and it is to be understood that the terminology used is 3. Weber F et al (1996) Hum Mol Genet 5:771-77.
4. Li H H et al (1999) Proc Natl Acad Sci USA 96:14505-10.
5. O'Brien J S (1972) Proc Natl Acad Sci USA 69:1720-22.
6. Kleijer W J et al (1996) Prenat Diagn 16:829-35.
7. March J and Fensom A H (1985) Clin Genet 27:258-62.
8. Hopwood J J (2005) Prenat Diagn 25:148-50.
9. He W et al (1994) Prenat Diagn 14:17-22.
10. Nowakowski R W et al (1989) Pediatr Res 26: 462-66.
11. Shapiro E G et al (1995) J Inheri Metab Dis 18:413-29.
12. Peters C et al (1998) Blood 91:2601-08.

13. Hoogerbrugge P M et al (1991) Bone Marrow Transplant 7:Suppl 2:71.
14. Hall J M et al (1995) Blood 86:2829-32.
15. Bianchi D W et al (1996) Proc Natl Acad Sci USA 93:705-08.
16. Simpson J L and Elias, S (1993) JAMA 270:2357-61.
17. Zilliacus R et al (1975) Scand J Haematol 15:333-38.
18. Khosrotehrani K et al (2004) JAMA 292: 75-80.
19. Lo Y M D et al (1996) Blood 88:4390-95.
20. Petit T et al (1997) Br J Haematol 98:767-71.
21. Marleau A M et al (2003) Lab Invest 83: 673-81.
22. Wan W et al (2002) Immunology 107:261-67.
23. Veenstra Van Nieuwenhoven A L (2003) Hum Reprod Update 9:347-57.
24. Trundley A and Moffett A (2004) Tissue Antigens 63:1-12.
25. Mellor A L and Munn D H (2000) Ann Rev Immunol 18:367-91.
26. Ando T and Davies T F (2003) J Clin Endocrinol Metab 88:2965-71.
27. Johnson K L et al (2001) Arthritis Rheum 44:1848-54.
28. Mikami T (2002) Med Electron Microsc 35:96-101.
29. Nayar B et al (2002) Int J Gynaecol Obstet 79:31-32.
30. Todaro A M et al (2000) Blood Purif 18:144-47.
31. Broxmeyer H E et al (1989) Proc Natl Acad Sci USA 86:3828-32.
32. Gluckman E et al (2005) Semin Hematol 42:85-90.
33. Thomson B G et al (2000) Blood 96:2703-11.
34. Staba S L et al (2004) N Engl J Med 350:1960-69.
35. Garbuzova-Davis S et al (2005) Stem Cells & Dev 14:384-94.
36. Ward J M and Devor-Henneman D E (2000) Gestational mortality in genetically engineered mice: evaluating the extraembryonal embryonic placenta and membranes. In PATHOLOGY OF GENETICALLY ENGINEERED MICE (Ward J M et al, eds) pp 103-22, Iowa State University Press, Ames, Iowa.
37. Coop A J (1995) Trends Genet 11:87-93.
38. Lo E S F et al (1998) Br J Haematol 100:605-06.
39. Stevens A M et al (2003) Lancet 362:1617-23.
40. Kaufman M H (2001) THE ATLAS OF MOUSE DEVELOPMENT. 525 pp. Academic Press, San Diego, Calif.
41. Garbuzova-Davis S et al (2003) J Hematother & Stem Cell Res 12:255-70.
42. Muntener M and Hsu Y-C (1977) Acta Anat 98:241-52.
43. Jones C J et al (1990) Placenta 11:395-411.
44. Ceuterick C et al (1980) Neuropediatrie 11:176-85.
45. Georgiades P et al (2002) Placenta 23:3-19.
46. Adamson S L et al (2002) Dev Biol 250:358-73.
47. Burton G J (1987) Scanning Microsc 1:1811-28.
48. Pijnenborg R et al (1981) Placenta 2:71-92.
49. Bulmer J N et al (1988) Placenta 9:238-46.
50. Gografe S I et al (2003) Comp Med 53:622-32.
51. Yu G et al (2004) Brain Res 1018:32-37.
52. Ibarra A et al (2003) Brain Res 979:165-78.
53. Keep M et al (2001) Brain Res 894:327-31.

What is claimed is:

1. A method of treating a fetus or embryo suspected of having a congenital condition, the method comprising the steps of
   providing a plurality of human umbilical cord blood cells in a form suitable for intravenous administration; and
   administering the human umbilical cord blood cells to a mother carrying a fetus or embryo suspected of having said congenital condition;
   wherein the congenital condition is Sanfilippo syndrome.

2. The method of claim 1, wherein the human umbilical cord blood cells are mononuclear cells.

3. The method of claim 1, further comprising the step of administering an immunosuppressant.

4. The method of claim 3, wherein the immunosuppressant is selected from cyclosporine A or tacrolimus.

5. The method of claim 1, wherein the administration of cord blood cells comprises administration of more than 3 million cells or 3 million cells.

6. The method of claim 1, wherein the administration of cord blood cells comprises the administration of about 9 million cells or 9 million cells.

7. The method of claim 1 wherein the human umbilical cord blood cells are administered intravenously.

8. The method of claim 1 wherein the human umbilical cord blood cells are administered intrauterinely.

9. The method of claim 1 wherein the human umbilical cord blood cells are administered intravaginally.

10. The method of claim 1 wherein the human umbilical cord blood cells are administered at day 5 of gestation.

* * * * *